United States Patent
Shank

(10) Patent No.: US 6,583,172 B1
(45) Date of Patent: Jun. 24, 2003

(54) ANTICONVULSANT DERIVATIVES USEFUL IN TREATING CHRONIC NEURODEGENERATIVE DISORDERS

(76) Inventor: Richard P. Shank, 551 Village Cir., Blue Bell, PA (US) 19422-1636

( * ) Notice: Subject to any disclaimer, the term of this patent is extended or adjusted under 35 U.S.C. 154(b) by 0 days.

(21) Appl. No.: 09/538,815

(22) Filed: Mar. 30, 2000

Related U.S. Application Data

(60) Provisional application No. 60/128,297, filed on Apr. 8, 1999.

(51) Int. Cl.[7] .................. A61K 31/385; A61K 31/35; A61K 31/335; C07F 5/02; A61N 41/02
(52) U.S. Cl. .................. 514/439; 514/455; 514/459; 514/463; 514/600; 562/37
(58) Field of Search ................ 514/439, 455, 514/459, 463, 600; 562/37; 558/48

(56) References Cited

U.S. PATENT DOCUMENTS

| | | | |
|---|---|---|---|
| 5,242,942 A | * | 9/1993 | Costanzo et al. |
| 5,258,402 A | * | 11/1993 | Maryanoff |
| 5,731,348 A | | 3/1998 | Gu et al. .................. 514/561 |
| 6,323,236 B2 | * | 11/2001 | McElroy |

FOREIGN PATENT DOCUMENTS

| | | | |
|---|---|---|---|
| WO | 94/14827 | * | 7/1994 |
| WO | 95/17406 | * | 6/1995 |
| WO | 97/13510 | * | 4/1997 |
| WO | 98/00123 | | 1/1998 |
| WO | 98/00124 | | 1/1998 |
| WO | 98/00131 | | 1/1998 |
| WO | 00/01376 | | 1/2000 |
| WO | 00/50020 | * | 8/2000 |

OTHER PUBLICATIONS

Angehagen, Mikael Et Al. "Does topiramate (TPM) have protective effects on astroglia cells and neurons in primary cortical cultures." Epilepsia, (1998) vol. 39, No Suppl 6, pp. 44 XP000923162 abstract 2.050.

B. Meldrum Et Al. "Excitatory amino acid neurotoxicity and neurodegenerative disesase" TIPS, vol. 11, 1990, pp. 379–387, XP000915223 the whole document.

Y. Yang Et Al. "Neuroprotection by delayed administration of topiramate in rat model of middle cerebral artery embolization" Brain Research, vol. 804, No. 2, 1998, pp. 169–176, XP000921218, the whole document.

* cited by examiner

*Primary Examiner*—Paul J. Killos
(74) *Attorney, Agent, or Firm*—Ralph R. Palo

(57) ABSTRACT

Anticonvulsant derivatives useful in treating chronic neurodegenerative conditions are disclosed.

4 Claims, 3 Drawing Sheets

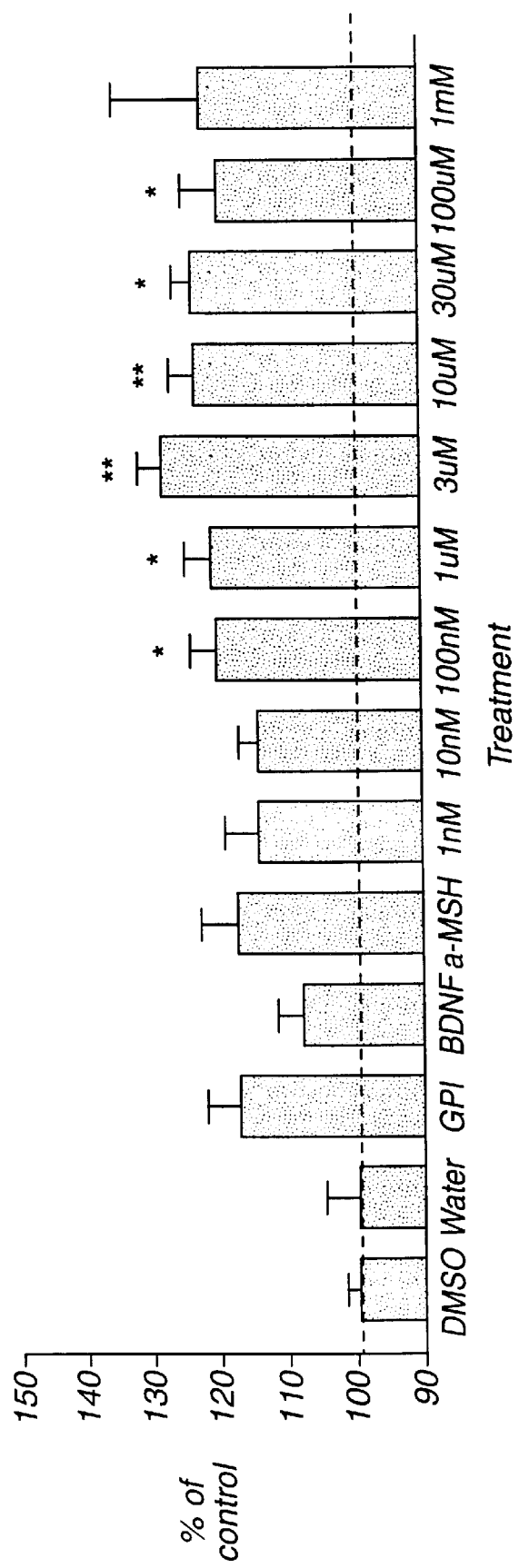

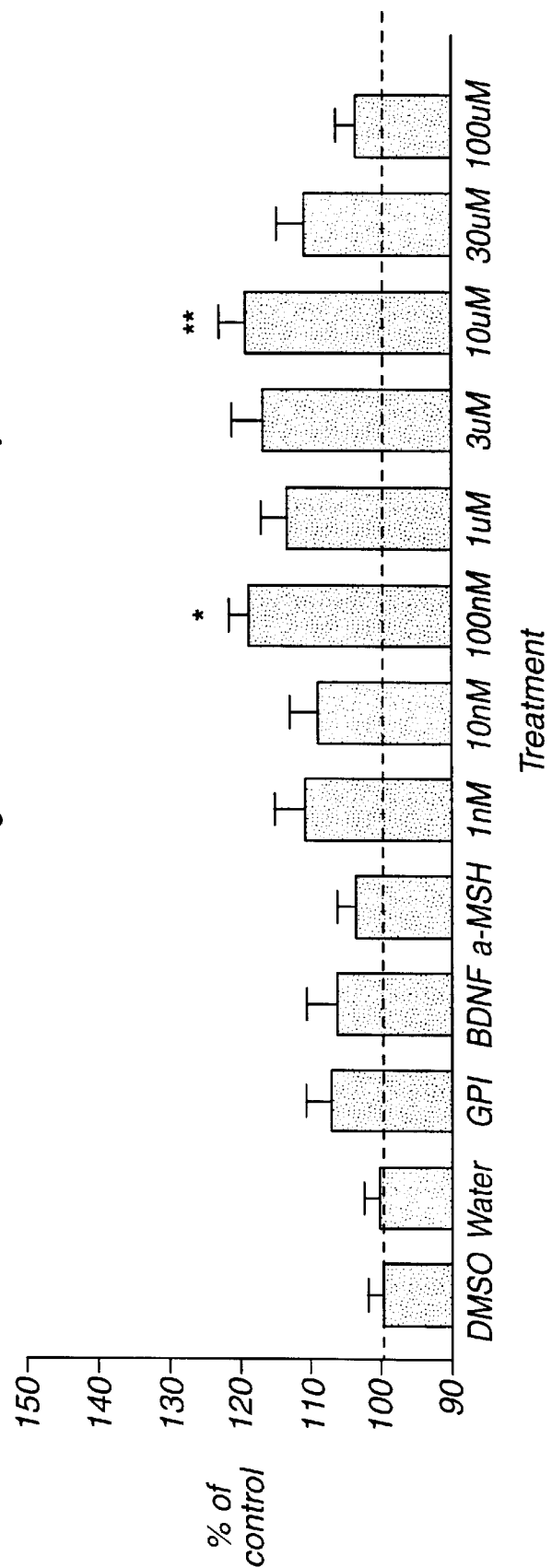

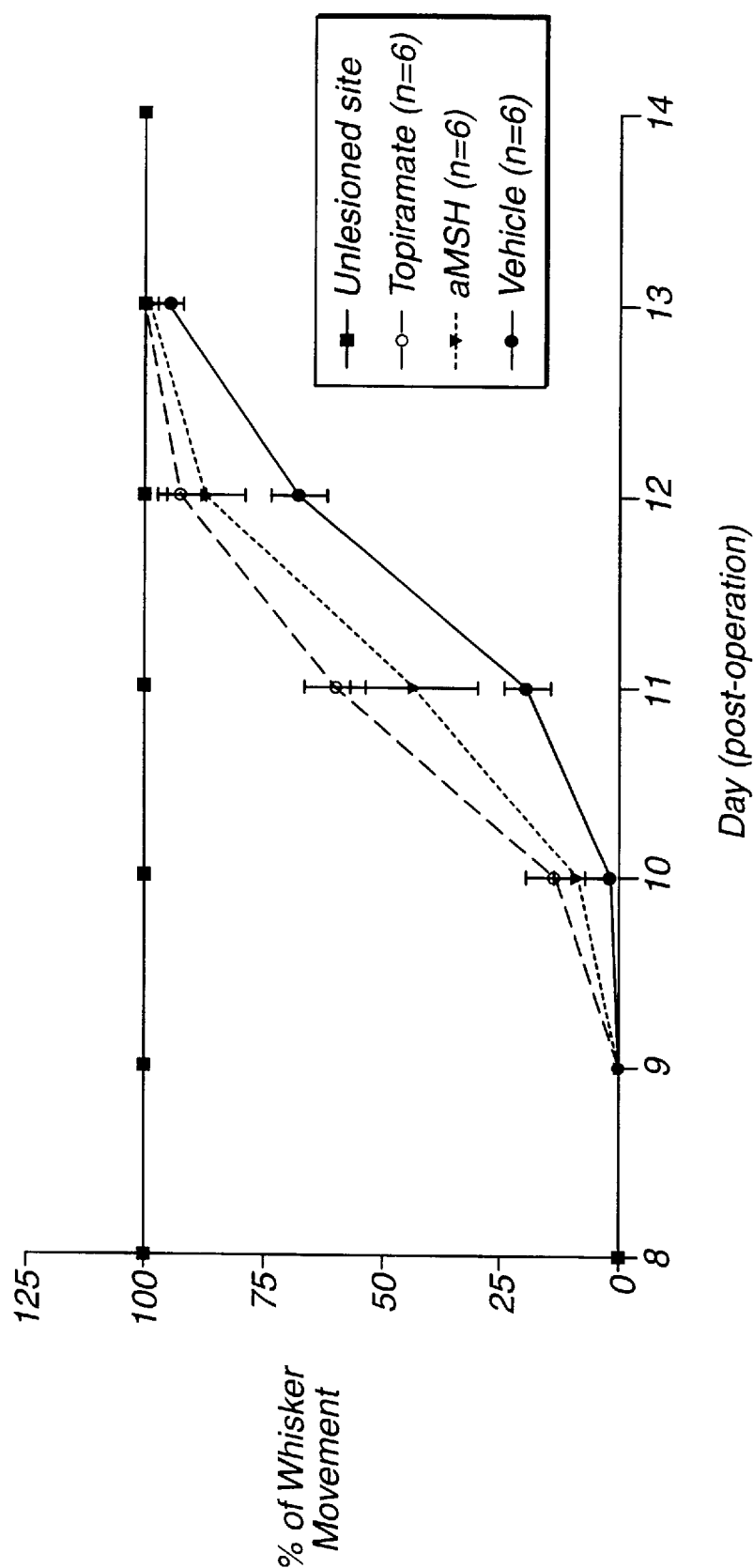

ANTICONVULSANT DERIVATIVES USEFUL IN TREATING CHRONIC NEURODEGENERATIVE DISORDERS

This application claims the benefit of provisional application Ser. No. 60/128,297, filed Apr. 8, 1999.

BACKGROUND OF THE INVENTION

Compounds of Formula I:

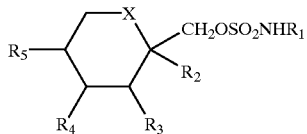

are structurally novel antiepileptic compounds that are highly effective anticonvulsants in animal tests (Maryanoff, B. E., Nortey, S. O., Gardocki, J. F., Shank, R. P. and Dodgson, S. P. *J Med. Chem*. 30, 880–887, 1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993). These compounds are covered by three U.S. Pat. Nos.: 4,513,006, 5,242,942, and 5,384,327. One of these compounds 2,3:4, 5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33, 1995; S. K. SACHDEO, R. C. SACHDEO, R. A. REIFE, P. LIM and G. PLEDGER, Epilepsia 36 (S4) 33, 1995), and is currently marketed for the treatment of simple and complex partial seizure epilepsy with or without secondary generalized seizures in approximately twenty countries including the United States, and applications for regulatory approval are presently pending in several additional countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89, 1994), and in an animal model of kindled epilepsy (A. WAUQUIER and S. ZHOU, Epilepsy Res. 24 73–77, 1996).

Recent preclinical studies on topiramate have revealed previously unrecognized pharmacological properties which suggest that topiramate should be effective in treating some other neurological disorders. One of these is chronic neurodegenerative disorders such as Alzheimer's disease, Parkinson's disease, Huntington's disease, multiple sclerosis, diabetic neuropathies, retinopathy, peripheral nerve injury and brain and spinal neurodegeneration arising as a result of head trauma or spinal injury.

DISCLOSURE OF THE INVENTION

Accordingly, it has been found that compounds of the following formula I:

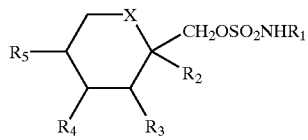

wherein X is O or $CH_2$, and R1, R2, R3, R4 and R5 are as defined hereinafter are useful in treating chronic neurodegenerative conditions, such as occurs in Alzheimer's disease, Parkinson's disease, Huntington's disease, multiple sclerosis, diabetic neuropathies, retinopathy, peripheral nerve injury and brain and spinal neurodegeneration arising as a result of head trauma or spinal injury.

DETAILED DESCRIPTION OF THE PREFERRED EMBODIMENTS

The sulfamates of the invention are of the following formula (I):

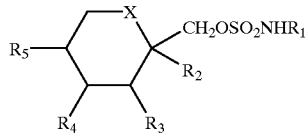

wherein
  X is $CH_2$ or oxygen;
  $R_1$ is hydrogen or alkyl; and
  $R_2$, $R_3$, $R_4$ and $R_5$ are independently hydrogen or alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

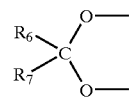

wherein
  $R_6$ and $R_7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =C—CH=CH—CH=.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium α-butoxide or sodium hydride at a temperature of about −20° to 25° C. and in a solvent such as toluene, THF or dimethylformamide wherein R is a moiety of the following formula (III):

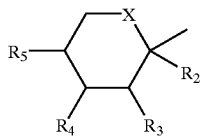

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of about 40° to 25° C. in a solvent such as methylene chloride or acetonitrile to produce a compound of formula (I). The reaction conditions for (b) are also described by T. Tsuchiya et al. in Tet. Letters, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in Tet. Lett. p. 2455–2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are identical and are of the formula (II) may be obtained by the method of R. F. Brady in Carbohydrate Research, Vol. 14, p. 35 to 40 (1970) or by reaction of the trimethylsilyl enol ether of a $R_6COR_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Volaa 38, No. 22, p. 3935 (1973).

Further, carboxylic acids and aldehydes of the formulae RCOOH and RCHO may be reduced to compounds of the formula RCH2OH by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I: may also be made by the process disclosed in U.S. Pat. Nos. 4,513,006, 5,242,942, and 5,384,327, which are incorporated by reference herein.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygen of the methylenedioxy group (II) are attached on the same side of the 6-membered ring.

The ability of the compounds of formula I to treat chronic neurodegenerative disorders is based from the results of studies in which topiramate was found to promote neurite outgrowth in neuronal cells in culture and to enhance nerve regeneration and recovery of function after injury in vivo In studies in vitro, cultures of rat hippocampal and cerebral cortical cells were established from embryonic day 18 pups. The cells were grown in culture wells (plates) for seven days in the presence of various concentrations of topiramate (0.1 nM–100 nM), or the neurotrophic factors BDNF (brain-derived neurotrophic, 10 ng) and α-MSH (alpha-melanocyte stimulating hormone, 50 nM), or vehicle (isotonic saline). Each compound was added to the culture medium in a specified set of wells at the time the cells were plated and then again four days later when the culture media was removed and replaced with fresh media. On the seventh day in culture, the cells were treated with formalin, a tissue fixative. Subsequently, the cells were treated with a fluorescein-labeled antibody specific for microtubule associated protein-2 (MAP-2), a selective marker for dendritic processes. The amount of fluorescein-labeled antibody bound to MAP-2 (FITC signal) in each well was analytically determined. This information was then used to calculate the relative degree of neurite outgrowth for the cells in each well. When compared to cells grown in medium containing only vehicle, the topiramate-treated cells exhibited a significantly higher level of FITC signal, thereby indicating that topiramate induced an increase in neurite outgrowth. For hippocampal cells, the increase was significantly higher ($P<0.05$) at concentrations ranging from 100 nM to 100 μM (FIG. 1).

FIG. 1 is a bar graph illustrating the effects of topiramate, BDNF,α-MSH and GPI on neurite outgrowth in rat hippocampal cell cultures, as measured by MAP-2 immunofluorescence. Neurite (dendrites and axons) outgrowth for control cell culture samples (DMSO or water) was assigned a value of 100, and neurite outgrowth for cell culture samples containing topiramate (10 nM to 1 mM) or a specified growth factor is shown as a percent ±SEM of the control values. The asterisks signify topiramate-treated samples that were significantly different from control samples: *$p<0.05$, **p0.01. However, a clear concentration-response effect was not observed.

For cortical cells a significant increase was observed at 100 nM (119% of control) and 10 μM (119% of control) ($p<0.05$). No dose-response relationship was evident, but topiramate treatment resulted in a modest increase in neurite outgrowth at most concentrations studied (range=106% to 119% of control).

FIG. 2 is a bar graph illustrating the effects of topiramate, BDNF,α-MSH and GPI on neurite outgrowth in rat cerebral cortical cell cultures, as measured by MAP-2 immunofluorescence. Neurite (dendrites and axons) outgrowth for control cell culture samples containing topiramate (10 nM to 100 uM) or a specified growth factor is shown as a percent ±SEM of the control values. The asterisks signify topiramate-treated samples that were significantly different from control samples: *$p<0.05$,**p0.01.

In the study in vivo, topiramate was evaluated in a rat facial nerve compression model of peripheral nerve injury. Rats were anesthetized, their skin and muscle excised to visualize the facial nerve. The nerve was injured near the stylom by compression with forceps. The wound was sutured and the rat allowed to recover before compound administration. The rats were divided into three groups: vehicle-treated, topiramate-treated (p.o., 20 mg/kg) and α-MSH-treated (s.c., 1 mg/kg). Compounds were administered twice daily for 14 days post-surgery. Facial nerve compression causes paralysis of the whisker muscle ipsilateral to the injury site. Restoration of whisker movement (lesioned versus non-lesioned side) was monitored daily for 14 days. Spontaneous recovery of whisker movement was detected as early as 10 days post-surgery with full recovery achieved by 13 days. On days 11 and 12 the degree of whisker movement recovery was significantly higher for the topiramate-treated group of rats than for the vehicle-treated group (day 11% recovery; topiramate=60%, vehicle=19%; p<0.001) (day 12 recovery; topiramate=92%, vehicle=68%, p<0.01). By comparison, the α-MSH treated group exhibited a smaller, statistically nonsignificant increase in recovery at days 11 and 12 (FIG. 3).

FIG. 3 is a line graph illustrating the effects of topiramate and α-MSH on the restoration of facial nerve function in rats, as measured by the rate whisker movement. The total rate of whisker movement on the side that the facial nerve was not injured was assigned a value of 100. Whisker movement on the side of the injured nerve is presented as a percent ±SEM of the whisker movement on the non-injured side. The rate of whisker movement was monitored visually by a skilled observer blinded to the treatment each rat received.

For treating chronic neurodegenerative conditions, topiramate or another compound of formula (I) may be employed by administering repeated oral doses in the range of about 16 to 256 mg once or twice daily.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., i.v. Sterile injectable formulations will be prepared using appropriate solubilizing agents. A unit dose would contain about 10 to 100 mg of the active ingredient. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

What is claimed is:

1. A method for treating chronic neurodegeneration comprising administering to a mammal afflicted with such condition a therapeutically effective amount of a compound

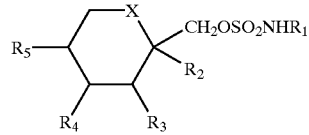

of the formula I:
wherein
    X is $CH_2$ or oxygen;
    $R_1$ is hydrogen or alkyl; and
    $R_2$, $R_3$, $R_4$ and $R_5$ are independently hydrogen or alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

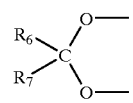

wherein
    $R_6$ and $R_7$ are the same or different and are hydrogen, lower alkyl or are alkyl and are joined to form a cyclopentyl or cyclohexyl ring.

2. The method of claim 1 wherein the compound of formula I is topiramate.

3. The method of claim 1, wherein the expected therapeutically effective amount is from about 32 to 512 mg.

4. The method of claim 1, wherein the dose amount for oral administration is of from about 16 to 256 mg.

* * * * *